United States Patent [19]

Taylor, Jr. et al.

[11] Patent Number: 5,009,889
[45] Date of Patent: Apr. 23, 1991

[54] TREATMENT OF DYSFUNCTIONAL VASCULAR ENDOTHELIUM USING ACTIVATED PROTEIN C

[75] Inventors: Fletcher B. Taylor, Jr.; Charles T. Esmon, both of Oklahoma City, Okla.

[73] Assignee: Oklahoma Medical Research Foundation, Oklahoma City, Okla.

[21] Appl. No.: 139,922

[22] Filed: Dec. 31, 1987

[51] Int. Cl.$^5$ .................... A61K 37/547; A61K 37/02
[52] U.S. Cl. .................................. 424/94.64; 514/2; 435/219; 435/226
[58] Field of Search ................. 514/2; 424/101, 94.64, 424/529; 435/219, 226

[56] References Cited

U.S. PATENT DOCUMENTS 4,775,624 10/1988 Bang et al. .......................... 435/226

FOREIGN PATENT DOCUMENTS 0191606 8/1986 European Pat. Off. .

OTHER PUBLICATIONS

Nawroth et al., Biol. Abstracts vol. 81, 99124 (6/1986).
Coleman, R. W., et al., *Controversy in Internal Medicine II*, pp. 633-648 (W. B. Saunders Company, 1974).
Niklasson, P. M., et al., Scand J. Inject. Dis. 4: 183-191 (1972).
Lerner, R., et al., *Am. Journal Obst. & Gynecology* 97, No. 3, pp. 373-378 (Feb. 1987).
Gallup, D. G., et al., *Obstetrics and Gynecology*, vol. 35, No. 5 pp. 690-695 (May 1970).
Corrigan, J. J., et al., *Am. J. Dis. Child*, vol. 126, pp. 629-632 (Nov. 1973).
Corrigan, J. J., *The Journal of Pediatrics*, vol. 91, No. 5, pp. 695-700 (Nov. 1977).
T. Yamakawa, "White Blood Cell Plugging and Blood Flow Maldistribution in the Capillary Network of Cat Cerebral Cortex in Acute Hemorrhagic Hypotension: An Intravital Microscopic Study", Circulatory Shock, 22:323-332 (1987).
G. Feuerstein et al., "Cellular and Humoral Interactions in Acute Microvascular Injury: A Pivotal Role for the Endothelial Cell", Critical Care: State of the Art (Soc. Crit. Care Med.; Fullterton, CA 1987) Chapter 5.
B. Braquet et al., "Platelet-Activating Factor and Cellular Immune Response", Immun. Today No. 11, 8:345-352 (1987).
C. T. Esmon et al., "Functions of the Protein C Anticoagulant Pathway: Modulation in Disease States", Current Adv. in Vitamin K Research, Steenbock Symposium held Jun. 21-25, 1987, pp. 85-96.
F. Walker et al., "Factors Involved in the Regulation of Protein S, a Cofactor Required for the Expression of the Activated Protein C Anticoagulant Activity", Current Adv. in Vitamin K Research, Steenbock Symposium held Jun. 21-25, 1987, pp. 101-108.
J. H. Griffin, "Protein C and Protein S Defects in Thromboembolic Disease", Current Adv. in Vitamin K Research, Steenbock Symposium held Jun. 21-25, 1987, pp. 97-100.
J. Stenflo et al., "Hydroxylated Aspartic Acid and Asparagine Residues in the Regions Homologous to the Epidermal Growth Factor Precursor in Protein C and Protein S", Curr. Adv. in Vitamin K Research, Steenbock Symposium held Jun. 21-25, 1987, pp. 109-120.
C. T. Przysiecki et al., "Post-translational Hydroxylation of Asparagine Residues in Protein S and Non-vitamin K-Dependent Proteins", Curr. Adv. in Vitamin K Research, Steenbock Symposium held Jun. 21-25, 1987, pp. 121-128.
K. Suzuki et al., "Interaction Site of Activated Protein C on Protein S", Curr. Adv. in Vitamin K Res., Steenbock Symposium Jun. 21-25, 1987, pp. 129-133.
J. Matschiner et al., "Heterogeneity of Protein C and Factor X from Human Plasma", Curr. Adv. in Vitamin K Res., Steenbock Symposium 6/21-25/87, pp. 135-140.
C. T. Esmon et al., "Protein C, Isolation and Potential Use in Prevention of Thrombosis", Dev. Biol. Stand. 67:51-57 (1987).
N. L. Esmon et al., "Analysis of Protein C and Protein S in Disease States", Dev. Biol. Standard 67:75-82 (1987).
C. T. Esmon et al., "Modulation of the Protein C Anticoagulant Pathway in Disease States", Steenbock Symposium, Curr. Adv. in Vitamin K Res., No. T-15 at 10, (Jun. 21-25, 1987).
J. Bhattacharya, "Sites of Transendothelial Liquid Transport in Lung Microcirculation", Fed. Proc. 46:2502-2505 (Jun. 1987).
D. M. Shasby et al., "Transendothelial Transfer of Macromolecules In Vitro", Fed. Proc. 46:2506-2510 (Jun. 1987).
P. Del Vecchio et al., "Endothelial Monolayer Permeability to Macromolecules", Federation Proc. 46:2511-2515 (Jun. 1987).
B. Meyrick et al., "Correlation of Permeability with the Structure of the Endothelial Layer of Pulmonary Artery Intimal Explants", Fed. Proc. 46:2516-2520 (Jun. 1987).

(List continued on next page.)

*Primary Examiner*—Jacqueline Stone
*Attorney, Agent, or Firm*—Kilpatrick & Cody

[57] ABSTRACT

A pharmaceutical composition comprising activated protein C activity is used to treat subjects for permeability and coagulopathic dysfunctions of vascular endothelial cells in response to an inflammatory stimulus. The composition may be used to prevent or to reverse these pathological events. Further, the composition is used to prevent elevated plasma levels of tumor necrosis factor, an inflammatory mediator which participates in the chain of events which produce the dysfunctional responses.

20 Claims, No Drawings

OTHER PUBLICATIONS

K. Dorovini-Zis et al., "Formation of a Barrier by Brain Microvessel Endothelial Cells in Culture", Fed. Proc. 46:2521-2522 (Jun. 1987).

F. B. Taylor et al., "Protein C Prevents the Coagulopathic and Lethal Effects of *E. coli* Infusion in the Baboon", J. Clin. Ivest. 79:918-925 (Mar. 1987).

M. Zoler, "Protein Holds Promise for Septic Shock Rescue", Med. World News, Jan. 26, 1987.

W. Rosenblum, "Biology of Disease: Aspects of Endothelial Malfunction and Function in Cerebral Microvessels", Lab. Invest. 55:252-268 (1986).

L. Maes et al., "Endothelial Injury and Platelet Thrombosis in Mesenteric Arteries of Rats: A Scanning Electron Microscopy Study", Blood Vessels, 23:1-8 (1986).

F. B. Taylor et al., "Activated Protein C Prevents *E. coli*-Induced Coagulopathy and Shock in the Primate:", Abs., Circulation, 74:Supp. 11-64 (Oct. 1986).

A. Lundwall et al., "Isolation and Sequence of the DNA for Human Protein S, a Regulator of Blood Coagulation", Proc. Natl. Acad. Sci., 83:6716-6720 (9/1986).

P. Nawroth et al., "Interleukin 1 Induces Endothelial Cell Procoagulant While Suppressing Cell-Surface Anticoagulant Activity", Proc. Natl. Acad. Sci., 83:3460-3464 (May 1986).

G. Grega, "Role of the Endothelial Cell in the Regulation of Microvascular Permeability to Molecules", Federation Proc. 45:75-76 (Feb. 1986).

F. Miller et al., "Contractile Elements in the Regulation of Macromolecular Permeability", Fed. Proc. 45:84-88 (Feb. 1986).

U. Ryan, "The Endothelial Surface and Responses to Injury", Fed. Proc. 45:101-108 (Feb. 1986).

B. Meyrick et al., "Direct Effects of *E. coli* Endotoxin on Structure and Permeability of Pulmonary Endothelial Monolayers and the Endothelial Layer of Intimal Explants", Am. J. Pathol. 122:140-151 (Jan. 1986).

G. Worthen et al., "Lung Vascular Injury Induced by Chemotactic Factors: Enhancement by Bacterial Endotoxins", Fed. Proc. 45:7-12 (Jan. 1986).

B. Meyrick, "Endotoxin-mediated Pulmonary Endothelial Cell Injury", Fed. Proc. 45:19-24 (Jan. 1986).

D. Kikeri et al., "Endotoxemic Acute Renal Failure in Awake Rats", Am. J. Phys. 250:F1098-F1106 (1986).

R. Rosenbaum et al., "Dexamethasone Inhibits Prostoglandin Release from Rabbit Coronary Microvessel Endothelium", Am. J. Physiol. 250:C970-C977 (1986).

R. J. Beckmann et al., "The Structure and Evolution of 461 Amino Acid Human Protein C Precursor and its Messenger RNA, Based Upon the DNA Sequence of Cloned Human Liver cDNAs", Nucl. Acids Research, 13:5233-5247 (1985).

F. B. Taylor et al., "Thrombin Activated Protein C Against Endotoxin", Abs., 8th Ann. Conf. on Shock, Baltimore, Maryland, (Jun. 9-12, 1985).

F. B. Taylor et al., "A Model for Thrombin Protection Against Endotoxin", Thromb. Res., 36:177-185 (1984).

M. B. Stemerman et al., "Perturbations of the Endothelium", Prog. in Hemostasis and Thrombosis (1984), pp. 289-324.

M. Reidy et al., "Recent Advances in Molecular Pathology: Arterial Endothelium-Assessment of In Vitro Injury", Exp. Mol. Path. 41:419-434 (1984).

H. Jacob, "The Role of Activated Complement and Granulocytes in Shock States and Myocardial Infarction", Clin. Med. 98:645-652 (1981).

A. Richman et al., "Peritubular Capillaries: A Major Target Site of Endotoxin-Induced Vascular Injury in the Primate Kidney", Lab. Invest. 43:327-332 (1980).

W. Kisiel, "Human Plasma Protein C: Isolation, Characterization and Mechanism of Activation by -Thrombin", J. Clin. Invest. 64:761-769 (1979).

J. J. Coalson et al., "A Morphologic Study of Live *E. coli* Organism Shock in Baboons", Exp. Mol. Pathol. 31:10-22 (1979).

J. Balis et al., "A Primate Model for Prolonged Endotoxin Shock: Blood-Vascular Reactions and Effects of Glucorticoid Treatment", Lab. Invest. 38:511-523, 1978.

E. Gaynor, "Vascular Lesions in Endotoxemia", Adv. in Exp. Med. and Biol. vol. 23 (Plenum Press, N.Y. 1972) at 337-345.

TREATMENT OF DYSFUNCTIONAL VASCULAR ENDOTHELIUM USING ACTIVATED PROTEIN C

FIELD OF THE INVENTION

The present invention relates to treatment of vascular endothelial cell dysfunction resulting from inflammatory conditions, and in particular to such treatment using a peptide having activated protein C activity.

SUMMARY OF THE INVENTION

The present invention comprises a pharmaceutical composition comprising an effective amount of a polypeptide characterized by activated protein C activity combined with a pharmaceutically acceptable carrier. This invention further comprises a method for preventing elevated plasma levels of tumor necrosis factor in a subject in need of such therapy. An effective amount of a pharmaceutical composition comprising a polypeptide characterized by activated protein C activity combined with a pharmaceutically acceptable carrier is administered to the subject.

The present invention comprises a method for inhibiting and for reversing the dysfunctional response of vascular endothelial cells to an inflammatory stimulus in a subject in need of such therapy. An effective amount of a pharmaceutical composition comprising a polypeptide characterized by activated protein C activity combined with a pharmaceutically acceptable carrier is administered to the subject.

DETAILED DESCRIPTION OF THE PREFERRED EMBODIMENT

Vascular endothelium is comprised of the epithelial cells that form the lining of blood vessels. While vascular endothelium once was thought to be a passive barrier which simply channeled the blood, it now is known that endothelial cells are actively involved in the regulation of intravascular coagulation mechanisms and in the movement of fluid between the parenchyma and the intravascular space.

Protein C is a vitamin K-dependent serine protease produced in an inactive form by the liver. The zymogen circulates in the plasma and is activated by thrombin only at the surface of endothelial cells. The activation occurs when protein C binds to the thrombin complexed to thrombomodulin on the endothelial cell surface. When so activated, the protein C-protein S complex deactivates two of the cofactors of the coagulant pathway, factors Va and VIIIa, thereby inhibiting coagulation.

Thus, the protein C pathway is one of the important mechanisms operating in the vascular endothelium to maintain the normal anticoagulant state of the endothelial surface. This and other anticoagulant mechanisms are necessary to prevent intravascular clotting, or thrombosis.

The endothelium of the microvasculature further normally functions as a dynamic semi-permeable membrane. Intracellular mechanisms selectively control the porosity of the cell to various blood components. Normally, the membrane of endothelial cells is permeable to certain small physiologic molecules, such as water and nutrients, and to larger molecules under selected conditions, allowing them to pass as needed to and from the adjacent tissues. However, the endothelium normally is impermeable to larger molecules, such as plasma proteins which must remain in the blood to function.

Although the endothelial mechanisms for regulating permeability and preventing thrombosis ordinarily are remarkably efficient, these mechanisms may be disrupted by an inflammatory stimulus which elicits the release of inflammatory mediators, and in particular the monokines tumor necrosis factor (TNF) and interleukin 1 (IL-1). In most cases, the release of these mediators is accompanied by activation of the plasma complement system.

An inflammatory stimulus which leads to release of inflammatory mediators occurs in a wide variety of pathological conditions. These conditions include sepsis, especially gram-negative septic shock, *staphylococcus aureus* septicemia, and injuries involving substantial tissue damage, such as burns and crush injuries. Such a stimulus also may occur in adult respiratory distress syndrome and reperfusion inflammatory syndrome.

The endothelial cell surface is converted from an anticoagulant to a procoagulant state which permits intravascular coagulation. This, in turn, leads to consumption of coagulation factors, hence the term consumption coagulation. When this dysfunction is systemic, it is referred to as disseminated intravascular coagulopathy (DIC).

The mechanisms for regulating permeability are affected so that the endothelial cell loses its ability to selectively control porosity. The endothelial cells swell and fluid begins leaking into the surrounding tissues causing anoxia and parenchymal damage. This is accompanied by increased peripheral resistance, decreased venous return and in many instances, death due to shock.

In most instances, for example septic shock, the response of the endothelium to the inflammatory stimuli involves both coagulopathy and abnormal permeability. However, in some conditions, both these dysfunctional responses may not occur. For example, some conditions may involve primarily uncontrolled permeability with minimal or no significant coagulopathy.

Although the above described dysfunctional responses of endothelium to inflammatory stimuli are not yet fully understood, it is believed that several pathways are involved. These pathways are set in motion by the inflammatory stimulus and result in the release of several inflammatory mediators.

The stimulus activates circulating monocytes and the fixed tissue macrophages in the liver and the lungs. After a lag period of about two to four hours, these blood cells release the monokine inflammatory mediators tumor necrosis factor (TNF) and interleukin 1 (IL-1).

It is believed that with other mediators, TNF causes internalization of the thrombomodulin receptors and the protein S receptors on the endothelial cell surface and the expression there instead of receptors for tissue factor (TF). It is established that TF receptors activate clotting factors VII and X. Thus, the surfaces of the endothelial cells are converted from a normally anticoagulant state to a dysfunctional procoagulant state. Clotting at the cell surface begins and the available clotting factors are eventually consumed.

Endothelial cell permeability dysfunction in response to an inflammatory stimulus has been attributed to the influence of inflammatory mediators on the contractile and cytoskeletal components of the cells. It is believed that TNF may participate in the chain of events that produces this dysfunction.

The above pathways are consistent with the clinical picture of septic shock which is one example of the inflammatory stimulus to which the present invention is directed. The clinical course of septic shock has been characterized as a four stage process which is consistent with the above described pathophysiology. [J. Clin. Invest. 79:918-925 (1987)].

Stage I begins with the inflammatory stimulus, e.g., a lethal infusion of *Escherichia coli*, and continues for about 120 minutes. In this stage, the scavenger cells (monocytes and macrophages) and PMN leukocytes are activated and the inflammatory mediators (TNF, IL-1, free hydroxyl radicals, elastase and others) are released.

Next, Stage II begins and continues for about four hours, or from two to six hours after the insult. During this stage, the mediators cause the endothelial cells to become inflamed or perturbed converting them from an anticoagulant to a procoagulant state. Fibrinogen levels fall and fibrin degradation products increase. The fibrinolytic activity of whole blood increases markedly by one to two hours and then decreases almost immediately at three hours after the insult.

Stage III occurs at about six hours following the insult and continues for about four hours. In this stage, the endothelial cells lose their ability to selectively control permeability and fluid begins to leak into the tissues injuring target organs. Liver damage is reflected by a rising SGPT level. The plasma level of activated protein C and the platelet count decrease gradually during Stages I to III.

In the fourth and final stage, the parenchymal edema produces shunting, peripheral and eventually central anoxia, and decreased mean systemic arterial pressure. The platelet and protein C levels continue to fall. Death occurs typically about 24 to 32 hours after the insult.

Now it will be appreciated that activated protein C plays a crucial role in the normal functioning of endothelial cells. It is a potent anticoagulant by controlling the clotting factors V and VIII. Also, as shown in Example 3 below, activated protein C is characterized by the ability to prevent elevation of plasma levels of tumor necrosis factor. Accordingly, as used herein, the term activated protein C activity refers to the ability to inactivate factors Va and VIIIa and to prevent elevated plasma levels of TNF.

The present invention is directed to the treatment of dysfunctional endothelial cells wherein the endothelium is characterized by loss of selective permeability or wherein the subject experiences coagulation abnormalities of the type described, or both. Such treatment utilizes a pharmaceutical composition comprising a polypeptide characterized by activated protein C activity. Treatment in accordance with this invention includes the prevention of the dysfunctional inflammatory response by prophylactic use of the protein C composition in high risk subjects, or in those clinical settings where such dysfunction is imminent or likely. Further, treatment includes the therapeutic use of the protein C composition to rescue subjects from a dysfunctional response already in progress. This invention further comprises the use of the protein C composition to prevent elevation of plasma levels of tumor necrosis factor in response to inflammatory mediators.

In accordance with the present invention, a pharmaceutical composition first is prepared. The composition comprises a polypeptide having activated protein C activity. This polypeptide may consist of activated protein C isolated from plasma preferably of the same species as the subject to be treated. However, it should be noted that cross-reactivity between species has been demonstrated [J. Clin. Invest. 79:918-925 (1987)]. Therefore, protein C from a species other than the subject's species may be employed successfully if necessary.

A polypeptide having activated protein C activity first is produced. Protein C may be isolated from plasma or produced using recombinant DNA techniques.

A preferred method for the isolation of protein C from humans involves the use of a monoclonal antibody. This isolation procedure has been reported previously [Develop. Biol. Standard., 67:51-57 (1987)]. Briefly, the procedure involves batch adsorption and elution of plasma protein C on QAE sephadex, batch adsorption and elution of protein C on an immobilized $Ca^{2+}$ dependent monoclonal antibody, termed HPC-4, and separation of trace contaminant, primarily serium amyloid P on QAE sephadex. The yield of this procedure is 1-2 mg per liter and the preparation time is reduced to 1.5 days.

The protein C may be isolated to homogeneity from human plasma using a five step procedure including barium citrate adsorption and elution, ammonium sulfate fractionalization, DEAE-Sephadex chromotography, dextran sulfate agurose chromatography, and preparative polyacrylamide gel electrophoresis, as described by Kisiel [J. Clin. Invest. 64:761-769 (September, 1979)]. Using this procedure about 5 mg of protein may be obtained from about 15 liters of plasma.

Alternately, protein C may be obtained from commercial preparations containing human clotting factors. One suitable product is KONYNE, marketed by Cutter Laboratories of Berkeley, Calif. A preferred procedure for preparing activated protein C from KONYNE is described by Taylor, et al. [J. Clin. Invest. 79:918-925 (March, 1987)]. However, activated protein C prepared by this method is only about 50% to 60% as active as protein purified from fresh frozen plasma.

Given the relatively low yield and high cost of purification and isolation techniques, recombinant DNA technology offers a much preferred means of obtaining the protein. Such procedures have been developed and successfully employed by Eli Lilly Company (Indianapolis, Ind.), Zymogenetics (Seattle, Wash.), and Integrated Genetics (Boston, Mass.).

For maximum activity, the protein should be used fresh, or within about five days if stored at 4° Centigrade. Alternately, the protein can be lyophilized and stored under refrigeration (4° C.). The protein can be stored in frozen solution, but the frozen solution may lose some of its activity.

Further techniques whereby peptides may be artificially manufactured based on active or key amino acid sequences or fragments may prove useful in producing polypeptides characterized by activated protein C activity. Therefore, it will be understood that any peptide having activated protein C activity, as that term is defined herein, may be used to practice this invention. This is so whether the polypeptide is produced artificially or from natural sources and regardless of whether it is structurally identical to the naturally occurring protein or any fragment thereof.

Having obtained a substantially pure preparation of a polypeptide characterized by activated protein C activity, this preparation next is combined with an acceptable pharmaceutical carrier. In the preferred embodiment, the preparation will be administered intravenously and the carrier should be selected accordingly. Preferred carriers include normal saline, five percent dextrose in water, Lactated Ringer's Solution and other commercially prepared physiological buffer solutions for intravenous infusion. Of course, the selection of the carrier may depend on the subject's needs or condition.

As demonstrated in the examples below, intravenous administration of the preparation usually will involve boluses of several milligrams each in conjunction with a continuous infusion of a more dilute solution. The concentration of the dilute solution may be adjusted to accommodate the fluid needs of the patient. In most instances, the desired administration rate for the protein will range from 8–32 μg/kg/min and may range as low as 2 μg/kg/min to as high as 64 μg/kg/min. Boluses typically will range from 1–10 mg, and preferably from 2–5 mg. These ranges are for guidance only. The response of the subject will be the primary determinant and this may vary widely depending on the particular needs of the subject and the inflammatory event involved. However, it will be noted that in general, rescue or therapeutic doses will be higher than doses required in prophylactic treatment.

The pharmaceutical composition described may be employed in a method for preventing elevation of plasma levels of tumor necrosis factor in a subject in need of such therapy. An effective amount of the composition is administered to the subject, preferably as described above. Preferably, a continuous intravenous infusion is begun at the rate of about 8 to 32 μg/k/body weight)/min. The subject's response will be monitored and the protein C administration rate adjusted accordingly.

Ideally, the subject's response would be monitored by regularly measuring the plasma levels of TNF, and an assay for TNF is set out below. However, this assay takes at least about 36 hours and thus, is not rapid enough to be of value in the clinical management of a subject undergoing the present treatment.

The subject's TNF activity may be measured. L929 cells (Memorial Sloan Kettering) are seeded at $2 \times 10^5$ cells/ml overnight as monolayers in microtiter plates. The test samples are diluted two-fold across the plate, UV irradiated, and then added onto the prepared cell monolayers. The culture media in the wells are then brought to 1 μg/ml actinomycin D. The plates are incubated for 18 hours at 37° C. and the plates are scored visually under the microscope. Each well is given a 25, 50, 75, or 100% mark signifying the extent of cell death in the well. One unit of TNF is defined as that reciprocal of the dilution at which 50% cytotoxicity occurs.

Until a rapid and accurate TNF assay is available, the subject's response should be monitored by regularly measuring heart rate, temperature, mean systemic arterial pressure (MSAP), pulse pressure, fibrinogen level and platelet count. The fibrinogen level and platelet count are indicators of coagulation and may not vary abnormally in conditions where only the permeability dysfunction occurs.

It has been shown that maximum TNF levels occur within about the first 120 minutes after the inflammatory insult. If the insult is a modest one, that is, one in which a coagulaopathic response is not expected, the subject may be clinically stable within two to four hours. However, where a more serious condition is involved and coagulopathic dysfunction is likely, it may be advisable to continue the infusion for a much longer period, perhaps as long as 12–24 hours, or until the risk of coagulopathy has passed.

In any event, if signs of an inflammatory response occur, the infusion rate should be increased and perhaps a bolus given. If the clinical signs indicate stabilization of the subject's condition, the infusion rate may be gradually decreased. When the signs continue to be stable as the dosage is decreased, the infusion may be discontinued.

The pharmaceutical composition of this invention also may be used to inhibit and to reverse the dysfunctional inflammatory response of vascular endothelial cells to inflammatory stimuli in a subject in need of such therapy. An effective amount of the composition is administered to a subject in need of such treatment.

The composition preferably is administered intravenously, and preferably a combination of a dilute continuous infusion with boluses as needed, as described previously. In treating a subject to inhibit or to reverse the dysfunctional responses, the subject's clinical signs are measured regularly and the dosage of protein C adjusted accordingly, as is also described above.

As indicated, a preferred method for monitoring the coagulopathic dysfunction is frequent measurement of the subject's fibrinogen levels. Fibrinogen levels may be measured by thrombin clotting time expressed in percent of control, the normal level being 100% of control.

In those situations where a dysfunctional inflammatory response has not yet become clinically apparent but is expected to occur, such as in the first several hours of a serious crush or burn injury, continuous intravenous therapy may be initiated before the clinical signs indicate onset of coagulopathy or permeability dysfunction. The initial dosage preferably will be low, such as about 8 μg/kg/min. However, the subject should be monitored closely. If the fibrinogen level begins to fall, indicating onset of coagulation dysfunction, or the vital signs and blood pressure indicate onset of permeability dysfunction, the dosage should be increased and perhaps a bolus given, to quickly raise the plasma level of the protein. When the subject's clinical condition appears to stabilize, the administration rate may be gradually decreased, and finally discontinued, as described above.

When the subject is in shock or other signs or symptoms, such as a falling fibrinogen level, indicate that a dysfunctional response already is in progress, the treatment method would be the same except that the initial administration rate should be higher, preferably 16–32 μg/kg/min.

EXAMPLE 1

We have studied the role of activated protein C in preventing *E. coli* induced shock in baboons. [F. B. Taylor, et al., J. Clin. Invest. 79: 918–925 (March, 1987)]. As this study has been published, it will only be summarized here.

For this study, protein C (zymogen) was isolated from KONYNE (Cutter Laboratories, Berkeley, Calif.) using an affinity column filled with calcium-dependent monoclonal antibody to the protein, HPC-4. (We showed that protein prepared in this manner had 50% to 60% of the identical concentration of activated protein C purified from fresh-frozen human plasma.) The protein C was activated with bovine thrombin, and the activated protein C then was separated from the thrombin by chromatography.

The study had three parts. In the first part, we demonstrated the normal course of E. coli induced shock in five baboons. Infusion of E. coli only into these animals at concentrations of $4 \times 10^{10}$ organisms/kg(body weight) produced a shock state that was accompanied first by a decrease of the fibrinogen level to 20% of control at T+360 (360 minutes following commencement of E. coli infusion) and then an increase in the SGPT level (a measure of liver cell injury) above the normal range. During the same period, protein C levels gradually declined to 50% to 40% of control at T+600.

Leukocyte and platelet counts dropped as did the MSAP (mean systemic arterial pressure). Death ensued at about 24 to 32 hours. This response and the post mortem findings are consistent with previous reports and mimic the clinical progression of sepsis and shock in humans.

In the second part of our study, we infused the same dose of E. coli, but also administered activated protein C with the organisms. In this model, the SGPT remained normal and protein C levels rose to a maximum of 816% of control at T-240. Although leukocyte and platelet levels fell, there was no sustained drop in MSAP. When the fibrinogen level fell to 75% to 70% of control, the infusion rate of activated protein C was increased so that the fibrinogen level never dropped below 70%. The activated protein C infusion rate ranged from the initial rate of 4 µg/kg/min. to as high as 64 µg/kg/min. A total of 7-8 mg/kg of the protein was infused over a period of 8 to 10 hours. All of these animals were permanent survivors.

Three other animals were given the same doses of E. coli and lower total activated protein C doses of 1, 3 and 4 mg/kg body weight over a shorter two-four hour period. In these animals, shock developed and the animals died in 24 to 32 hours. On the other hand, one animal which was given 10 mg/kg body weight of activated protein C over a two hour period survived. Thus, the necessary dosage appears to be a function of the amount of the protein as well as the period of time over which it is administered.

In the third part of the study, the protective role of activated protein C in the shock response was investigated. To do this, we blocked the activation of the animals' endogenous protein C by infusion of anti-protein C monoclonal antibodies prior to the infusion of E. coli. In these experiments, the same dose of E. coli produced a more severe response and quicker death in 16–24 hours. There was no shock in the animals infused with anti-protein C alone (without E. coli).

We next conducted tests to determine if in the absence of normal levels of endogenous activated protein C an otherwise non-lethal dose of E. coli would become lethal. To do this, we infused sub-lethal doses of E. coli (10% of the lethal concentration) with and without pre-infusion with the anti-protein C antibody. The animals not given the antibody exhibited a rise in fibrinogen and temperature and a fall in leukocytes, but they recovered and survived. On the other hand, in the animals given the antibody, the clinical signs were almost identical to those animals in the first part of the study which were given lethal doses of E. coli alone. Two of the three animals so treated were dead in about 32 hours.

Finally, to test the specificity of the effects of combining the sub-lethal E. coli and the antibody, we repeated these studies and included the infusion of activated protein C. This prevented the lethal effects and resulted in only a transient fall in leukocyte count as opposed to the sustained fall in the unprotected animals. All the animals so treated survived.

The above three-part study demonstrates that administration of activated protein C with lethal doses of E. coli will prevent the development of sepsis and death in the animals. The relatively high dose of the protein required may have been due at least in part to the fact that the protein was from a different species (human) and was derived from the less active KONYNE preparation. It is believed that in treating humans with human protein purified from plasma or prepared by recombinant DNA procedures, lower doses would be effective.

EXAMPLE 2

Having shown that infusion of activated protein C with infusion of lethal doses of E. coli would prevent the lethal effect of the organisms, [J. Clin. Invest. 79: 918-925 (March, 1987)], we next investigated what effect, if any, infusion of activated protein C would have on animals already in shock. These studies demonstrate that the administration of activated protein C during Stage II of the shock phase, after the endothelium has become perturbed, reverses the inflammatory response and rescues the animals from what otherwise would have been fatal sepsis.

Five baboons were infused with lethal doses of E. coli. Two to four hours later, the animals were infused with activated protein C. The protocol employed here was identical to that in the published study, described in Example 1, except that the activated protein C infusion was initiated after the onset of the inflammatory response, instead of with infusion of the organisms, and was continued over a longer period of time.

The course of one of the experiments is shown in Table I below. The E. coli infusion was begun at time 0. The response of the animal was monitored regularly by taking vital signs, temperature and MSAP. Also, the inflammatory and coagulopathic responses were monitored by measuring the plasma levels of white blood cells, fibrinogen and platelets. In the experiment shown in Table I, a continuous infusion of activated protein C was initiated at T+120, that is, two hours after the initiation of the infusion of organisms. By T+120, when the activated protein C infusion was begun, the fibrinogen level had dropped to 63% of normal.

Initially, activated protein C was administered at the rate of 16 µg/kg/min. The infusion rate was adjusted and boluses of activated protein C were given in response to the decreased fibrinogen level. The protein C infusion was decreased from 32 µg/kg/min. to 8 µg/kg/min. at T+270 to T+510 to determine how active the fibrinogen consumptive process was.

In the study shown in Table 1, the animal received an average of 16 µg/kg/min. over a 9½ hour period, two 3 mg boluses for a total dosage of 45 mg. The day following the experiment, the animal was alert and mobile and was a permanent survivor.

The results of the other four baboons studied are similar. The rate of the activated protein C infusion varied from 10 to 32 µg/kg/min with boluses of 2-5 mg during the peak of the inflammatory response. The total doses ranged from 45 to 150 mg, as compared to the 20 to 60 mg required in the reported prophylactic studies where the protein C infusion was started at the same time as the E. coli. It will be noted that in these therapeutic studies, a longer infusion period was used, about 10 to 12 hours, as compared to the 6 to 8 hours in the prophylactic studies.

All five of the animals tested survived the experiment and none developed septic shock, even though lethal doses of bacteria were given. However, two of the animals died of intussusception at two-five days. From these data, we concluded that although higher doses may be necessary, activated protein C is an effective treatment for sepsis. More particularly, we concluded that the administration of activated protein C can reverse what previously has been believed to be a fatal and non-reversible inflammatory response.

TABLE I

Effect of Activated Protein C to Rescue Animal with E. coli Induced Sepsis

| Comments | Time (min) | MSAP | HR | RESP | TEMP (R) °C. | FIBR * | Xa ** | HCT | WBC | PLTS |
|---|---|---|---|---|---|---|---|---|---|---|
| Began E. coli infusion of 4 × 10^10 organism/kg and cont'd for 120 min. | 0 | 100 | 120 | 15 | 36.3 | 100 | 33 | 45 | 9.9 | 169 |
|  | 60 | 90 | 170 | 30 | 36.3 | 68 | 39 | — | — | — |
| APC infusion begun at 16 μg/kg/min. | 120 | 45 | 190 | 30 | 36.8 | 63 | 63 | 45 | 1.4 | 150 |
|  | 135 | 75 | 170 | 30 | 36.8 | 62 | >300 | — | — | — |
|  | 150 | 65 | 190 | 30 | 36.8 | 57 | >300 | — | — | — |
| APC bolus of 3 mg (0.8 ml) | 165 | 65 | 190 | 30 | 36.8 | 55 | >300 | — | — | — |
| At T + 188, APC infusion inc'd to 32 μg/kg/min. | 180 | 55 | 240 | 30 | 36.8 | 55 | >300 | — | — | — |
|  | 195 | 55 | 210 | 30 | 36.8 | 51 | >300 | — | — | — |
| At T + 220, APC bolus of 3 mg (0.8 ml) | 210 | 55 | 200 | 30 | 36.8 | 42 | >300 | — | — | — |
|  | 225 | 50 | 210 | 30 | 36.9 | 42 | >300 | — | — | — |
|  | 240 | 70 | 210 | 30 | 36.9 | 36 | >300 | 48 | 2.4 | 145 |
|  | 255 | 60 | 210 | 30 | 36.9 | 36 | >300 | — | — | — |
| APC infusion dec'd to 8 μg/kg/min. | 270 | 65 | 210 | 30 | 36.9 | 40 | >300 | — | — | — |
|  | 285 | — | — | — | — | — | — | — | — | — |
|  | 300 | 70 | 210 | 30 | 36.9 | 36 | 220 | — | — | — |
|  | 315 | — | — | — | — | — | — | — | — | — |
|  | 330 | — | — | — | — | — | — | — | — | — |
|  | 360 | 70 | 200 | 30 | 36.8 | 33 | 182 | 48 | 2.0 | 172 |
|  | 420 | 70 | 210 | 30 | 36.8 | — | — | — | — | — |
| At T + 510, APC infusion inc'd to 16 μg/kg/min. | 480 | 68 | 210 | 30 | 37.0 | 25 | 190 | — | — | — |
|  | 540 | 65 | 210 | 30 | 37.2 | — | — | — | — | — |
| APC infusion dec'd to 8 μg/kg/min. | 600 | 60 | 210 | 30 | 37.3 | 25 | 215 | 46 | 2.1 | 45 |
|  | 660 | 60 | 210 | 30 | 37.3 | — | — | — | — | — |
| APC infusion disc'd | 690 | 60 | 210 | 30 | 37.3 | — | — | — | — | — |

*Fibrinogen expressed in percent of control;
**Factor Xa one-stage clotting assay expressed in seconds.

EXAMPLE 3

We next investigated what effect this protein has on plasma levels of tumor necrosis factor (TNF). Three baboons were tested. Each was given a lethal dose of E. coli over two hours as described in the previous examples. The first and third animals were nonsensitized, that is they had not been exposed previously to sub-lethal concentrations of E. coli. The second animal was sensitized. The third animal was given activated protein C together with a lethal dose of E. coli. About 8 mg/kg of body weight was administered over about 9 hours as described above, beginning at T+0.

The animals' TNF levels were measured at intervals, and the results are shown in Table II. These results show that in both the sensitized and unsensitized animals receiving E. coli, a sharp rise in TNF had occurred by the end of the second hour of the E. coli infusion. Both of these animals died of septic shock. On the other hand, only a minimal elevation of TNF is shown in the animal which also received activated protein C, and this animal was a permanent survivor.

Based on these data, we concluded that administration of activated protein C will inhibit the appearance of elevated levels of TNF in the plasma. TNF contributes to the inflammatory response of vascular endothelium to inflammatory stimuli such as E. coli infusions. Thus, we further concluded that activated protein C can be successfully employed to prevent or at least reduce the effects of TNF on endothelium experiencing an inflammatory insult.

TABLE II

Effect of Lethal E. coli Infusion on Plasma Levels of Tissue Necrosis Factor (TNF) With and Without Concomitant Infusion of Activated Protein C (APC)

| Time (hours) | TNF Levels (Units/ml) | | |
|---|---|---|---|
|  | Animal #1 (nonsensitized) | Animal #2 (sensitized) | Animal #3 (nonsensitized + APC) |
| 0 | 67 | 0 | 0 |
| 1 | 86 | 183 | 19 |
| 2 | 433 | 746 | 70 |
| 3 | 18 | 841 | 38 |
| 4 | 12 | 20 | 49 |
| 6 | 0 | 27 | 76 |
| 7 | — | — | 59 |
| 8 | — | 0 | — |
| 10 | — | 0 | 0 |
| 18 | 172 | — | — |
| 24 | 60 | — | — |

EXAMPLE 4

Another study was performed to investigate the effect of a sublethal dose of E. coli on plasma levels of TNF. An infusion of 0.4 × 10^10 organisms was administered over 120 minutes.

The baboon's TNF levels, white blood count and fibrinogen level, were measured at intervals and are shown in Table III. The TNF level did rise, but more slowly (at three to four hours) and to a much lesser extent than in the animals given lethal doses of the organisms (see data on Animals 1 and 2 in Table II from Example 3 above). However, it will be noted that there was no decrease in fibrinogen level.

The cardiovascular response during the first two to three hours, as measured by heart rate, blood pressure and pulse pressure, and the temperature rise, was identical to that demonstrated in animals given lethal doses of the organism. However, the animal experienced no end organ injury or coagulopathy, and recovered without treatment.

None of the physical parameters are a direct measurement of vascular endothelial permeability. However, it is established that increased permeability is associated with (1) elevated plasma levels of TNF and other inflammatory mediators, including platelet-activating factor (PAF); (2) decreases in white blood cell counts; and (3) margination of polymorphonuclear leukocytes. Further, the data from this study is consistent with experience in other animal models in which permeability was directly measured. [B. Meyrick and K. Brigham, Lab Invest. 48:458–570 (1983)].

TABLE III

Effect of Sublethal *E. coli* Infusion on Plasma Levels of Necrosis Factor (TNF), White Cells and Fibrinogen

| Time (hours) | TNF (units/ml) | White Cells (cells/mm$^3$) | Fibrinogen (% of control) |
|---|---|---|---|
| 0 | 0 | 7,200 | 100 |
| 1 | 0 | 1,100 | 100 |
| 2 | 0 | 1,600 | 100 |
| 3 | 52 | 2,500 | 100 |
| 4 | 20 | 6,000 | 122 |
| 6 | 0 | 8,000 | 138 |
| 10 | 0 | 12,200 | 162 |

Based on the foregoing, it now will be appreciated that the composition and methods of the present invention provide treatment of vascular endothelial cell dysfunction characterized by disturbances in coagulation or permeability controls which are induced by an inflammatory stimulus causing release of tumor necrosis factor and other inflammatory mediators. In one embodiment, the present invention provides life saving treatment to subjects suffering from inflammatory conditions which heretofore have been considered irreversible and usually fatal. In another embodiment, the present invention provides a method by which the inflammatory response can be prevented. In a still further embodiment, the composition of this invention is used to prevent elevation of plasma levels of a mediator, TNF, which contributes to the dysfunctional responses of endothelial cells.

Changes may be made in the nature, composition, operation and arrangement of the various elements, steps and procedures described herein without departing from the spirit and scope of the invention as defined in the following claims.

What is claimed is:

1. A pharmaceutical composition comprising:
   an effective amount of a polypeptide characterized by activated protein C activity to inhibit inflammatory stimuli disrupting cell permeability and normal coagulation processes in a patient suffering from a dysfunction of endothelial cells; and
   a pharmaceutically acceptable carrier.

2. A method for inhibiting the dysfunctional response of vascular endothelial cells to an inflammatory stimulus in a subject in need of such therapy, comprising:
   administering to the subject a pharmaceutical composition comprising an effective amount of a polypeptide characterized by activated protein C activity to inhibit the inflammatory stimuli in combination with a pharmaceutically acceptable carrier.

3. The method of claim 2 wherein the inflammatory stimuli include sepsis.

4. The method of claim 3 wherein the subject is a primate and between 2 and 64 μg APC/kg body weight is administered per minute.

5. The method of claim 2 wherein the subject is a primate.

6. A method for reversing the dysfunctional response of vascular endothelial cells to inflammatory stimuli in a subject in need of such therapy, comprising:
   administering to the subject a pharmaceutical composition comprising an effective amount of a polypeptide characterized by activated protein C activity to inhibit the inflammatory stimuli in combination with a pharmaceutically acceptable carrier.

7. The method of claim 6 wherein the subject is characterized by elevate plasma levels of tissue necrosis factor.

8. The method of claim 7 wherein the subject is a primate.

9. The method of claim 8 in which the inflammatory stimulus is sepsis.

10. The method of claim 6 wherein the dysfunctional response of the endothelial cells is characterized by abnormal permeability.

11. The method of claim 10 in which the subject is a primate and between 2 and 64 μg APC/kg body weight is administered per minute.

12. The method of claim 11 in which the inflammatory stimulus is sepsis further comprising administering a bolus of between 1 and 10 mg APC.

13. The method of claim 6 in which the subject is characterized by intravascular coagulopathy.

14. The method of claim 13 in which the subject is a primate and between 2 and 64 μg APC/kg body weight is administered per minute.

15. The method of claim 14 in which the inflammatory stimulus is sepsis.

16. The method of claim 2 wherein an effective amount of the pharmaceutical composition to prevent elevated plasma levels of tumor necrosis factor is administered to a patient.

17. The method of claim 6 wherein an effective amount of the pharmaceutical composition to prevent elevated plasma levels of tumor necrosis factor is administered to a patient.

18. The composition of claim 1 in a carrier suitable for intravenous administration, delivering between 2 and 64 μg APC/kg body weight/infused min.

19. The composition of claim 18 delivering between 8 and 32 μg APC/kg/min.

20. The composition of claim 1 delivering from 1 to 10 mg APC.

* * * * *

UNITED STATES PATENT AND TRADEMARK OFFICE
CERTIFICATE OF CORRECTION

PATENT NO.   : 5,009,889
DATED        : April 23, 1991
INVENTOR(S)  : Fletcher B. Taylor, Jr. and Charles T. Esmon It is certified that error appears in the above-identified patent and that said Letters Patent is hereby corrected as shown below:

Column 1,
Line 4, "The United States Government may have rights to this invention by virtue of National Institute of Health Grant No. R01GM37704."

Column 10,
Table II is split. Recombind as

Signed and Sealed this

Ninth Day of April, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 5,009,889
DATED : April 23, 1991
INVENTOR(S) : Fletcher B. Taylor, Jr. and Charles T. Esmon It is certified that error appears in the above-identified patent and that said Letters Patent is hereby corrected as shown below:

Column 1,
Line 4, insert -- The United States Government may have rights to this invention by virtue of National Institute of Health Grant No. R01GM37704. --

Column 10,
Table II is split. Recombind as

TABLE II
Effect of Lethal *E. coli* Infusion on Plasma Levels of Tissue Necrosis Factor (TNF) With and Without Concomitant Infusion of Activated Protein C (APC)

| Time (hours) | TNF Levels (Units/ml) | | |
|---|---|---|---|
| | Animal #1 (nonsensitized) | Animal #2 (sensitized) | Animal #3 (nonsensitized + APC) |
| 0 | 67 | 0 | 0 |
| 1 | 86 | 183 | 19 |
| 2 | 433 | 746 | 70 |
| 3 | 18 | 841 | 38 |
| 4 | 12 | 20 | 49 |
| 6 | 0 | 27 | 76 |
| 7 | — | — | 59 |
| 8 | — | 0 | — |
| 10 | — | 0 | 0 |
| 18 | 172 | — | — |
| 24 | 60 | — | — |

This certificate supersedes Certificate of Correction issued April 9, 2002.

Signed and Sealed this

Second Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 5,009,889
DATED        : April 23, 1991
INVENTOR(S)  : Fletcher B. Taylor, Jr. and Charles T. Esmon It is certified that error appears in the above-identified patent and that said Letters Patent is hereby corrected as shown below:

Column 1,
Line 4, insert -- The United States Government may have rights to this invention by virtue of one or more National Institute of Health Grants, including No. R01GM37704 to Fletcher B. Taylor Jr. and/or R37HL30340 to Charles T. Esmon. --

Column 10,
Table II is split. Recombine as

TABLE II

Effect of Lethal *E. coli* Infusion on Plasma Levels of Tissue Necrosis Factor (TNF) With and Without Concomitant Infusion of Activated Protein C (APC)

| Time (hours) | TNF Levels (Units/ml) | | |
|---|---|---|---|
| | Animal #1 (nonsensitized) | Animal #2 (sensitized) | Animal #3 (nonsensitized + APC) |
| 0  | 67  | 0   | 0  |
| 1  | 86  | 183 | 19 |
| 2  | 433 | 746 | 70 |
| 3  | 18  | 841 | 38 |
| 4  | 12  | 20  | 49 |
| 6  | 0   | 27  | 76 |
| 7  | --  | --  | 59 |
| 8  | --  | 0   | -- |
| 10 | --  | 0   | 0  |
| 18 | 172 | --  | -- |
| 24 | 60  | --  | -- |

This certificate supersedes Certificate of Correction issued July 2, 2002.

Signed and Sealed this

Seventeenth Day of September, 2002

Attest:

Attesting Officer

JAMES E. ROGAN
Director of the United States Patent and Trademark Office